United States Patent [19]
Hedgecock et al.

[11] Patent Number: 4,895,863
[45] Date of Patent: Jan. 23, 1990

[54] NOVEL IMIDAZO[2,1-B]BENZOTHIAZOLES

[75] Inventors: Charles J. R. Hedgecock, Wootton Bassett; David P. Kay, Swindon, both of Great Britain

[73] Assignee: Roussel Uclaf, Paris, France

[21] Appl. No.: 259,285

[22] Filed: Oct. 18, 1988

[30] Foreign Application Priority Data

Oct. 20, 1987 [GB] United Kingdom ............... 8724566

[51] Int. Cl.$^4$ .................. C07D 513/04; A61K 31/425
[52] U.S. Cl. .................................... 514/366; 548/149; 548/151
[58] Field of Search ............... 548/151, 149; 514/366

[56] References Cited

U.S. PATENT DOCUMENTS 4,464,384 8/1984 Murase .......................... 548/151

FOREIGN PATENT DOCUMENTS 149288 9/1982 Japan ............................. 548/151

OTHER PUBLICATIONS

Clement-Jewery, J. Med. Chem., 31, 1220, (1988).

Primary Examiner—Robert Gerstl
Attorney, Agent, or Firm—Bierman and Muserlian

[57] ABSTRACT

A compound selected from the group consisting of a compound of the formula

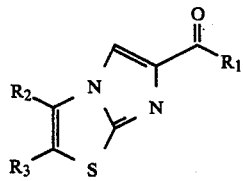

wherein $R_1$ is selected from the group consisting of

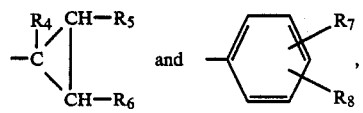

$R_4$, $R_5$, $R_7$ and $R_8$ are individually selected from the group consisting of hydrogen and alkyl of 1 to 5 carbon atoms, $R_6$ is selected from the group consisting of hydrogen, alkyl of 1 to 5 carbon atoms, phenyl, halogen, alkoxycarbonyl of 2 to 5 carbon atoms, cyano,

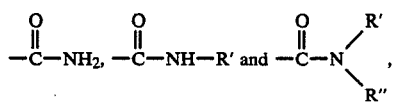

$R'$ and $R''$ are individually alkyl of 1 to 5 carbon atoms, $R_2$ and $R_3$ together form a member of the group consisting of

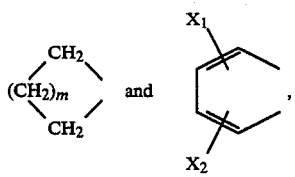

m is 1, 2 or 3, $X_1$ and $X_2$ are individually selected from the group consisting of hydrogen, alkyl of 1 to 5 carbon atoms, alkenyl of 2 to 5 carbon atoms, alkoxy of 1 to 5 carbon atoms, aralkoxy, aryloxy, halogen, azido and nitro or taken together form methylenedioxy and their non-toxic, pharmaceutically acceptable acid additon salts capable of treating memory disorders.

22 Claims, No Drawings

NOVEL IMIDAZO[2,1-B]BENZOTHIAZOLES

STATE OF THE ART

Commonly assigned U.S. Pat. No. 4,532,243 describes imidazopyrimidines having anxiolytic activity.

OBJECTS OF THE INVENTION

It is an object of the invention to provide the novel imidazo[2,1-b]benzothiazoles of formula I and their non-toxic, pharmaceutically acceptable acid addition salts and a novel process and novel intermediates.

It is another object of the invention to provide novel compositions and method for treating memory disorders.

These and other objects and advantages of the invention will become obvious from the following detailed description.

THE INVENTION

The novel compounds of the invention are compounds having a formula selected from the group consisting of a compound of the formula

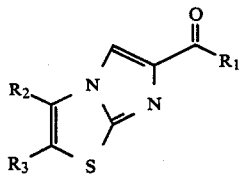
I wherein $R_1$ is selected from the group consisting of

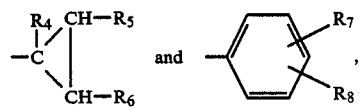

$R_4$, $R_5$, $R_7$ and $R_8$ are individually selected from the group consisting of hydrogen and alkyl of 1 to 5 carbon atoms, $R_6$ is selected from the group consisting of hydrogen, alkyl of 1 to 5 carbon atoms, phenyl, halogen, alkoxycarbonyl of 2 to 5 carbon atoms, cyano,

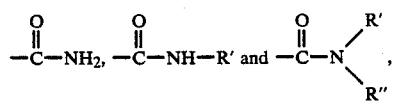

R' and R" are individually alkyl of 1 to 5 carbon atoms, $R_2$ and $R_3$ together form a member of the group consisting of

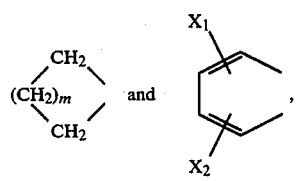

m is 1, 2 or 3, $X_1$ and $X_2$ are individually selected from the group consisting of hydrogen, alkyl of 1 to 5 carbon atoms, alkenyl of 2 to 5 carbon atoms, alkoxy of 1 to 5 carbon atoms, aralkoxy, aryloxy, halogen, azido and nitro or taken together form methylenedioxy and their non-toxic, pharmaceutically acceptable acid addition salts.

Examples of alkyl of 1 to 5 carbon atoms are methyl, ethyl, propyl, isopropyl, butyl, isobutyl, tert.-butyl and pentyl. Preferred halogens are fluorine, chlorine or bromine and examples of alkoxycarbonyl of 2 to 5 carbon atoms are methoxycarbonyl, ethoxycarbonyl and propoxycarbonyl. Examples of alkoxy of 1 to 5 carbon atoms are methoxy, ethoxy, propoxy and isopropoxy.

Examples of alkenyl of 2 to 5 carbon atoms are vinyl, allyl, but-3-enyl and isopropenyl. Examples of mono- and dialkylamido are methylamido, dimethylamido, ethylamido, diethylamido, propylamido and dipropylamido. Examples of aralkoxy are benzyloxy, phenethoxy or thienylmethoxy and examples of aryloxy are phenoxy and naphthoxy.

Examples of suitable acids for the non-toxic, pharmaceutically acceptable acid addition salts are inorganic acids such as hydrochoric acid, hydrobromic acid, hydriodic acid, nitric acid, sulfuric acid, phosphoric acid, and organic acids such as propionic acid, formic acid, benzoic acid, maleic acid, fumaric acid, succinic acid, tartaric acid, citric acid, oxalic acid, glyoxylic acid or aspartic acid, or alkanesulfonic acids such as methanesulfonic acid or arylsulfonic acids such as benzenesulfonic acid.

Among the preferred compounds of formula I are those wherein $R_1$ is

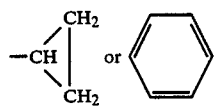

and $R_2$ and $R_3$ are

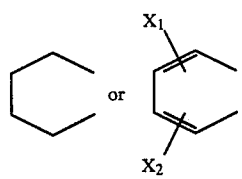

and $X_1$ and $X_2$ are individually hydrogen, methyl, methoxy, isopropoxy or benzyloxy and their non-toxic, pharmaceutically acceptable acid addition salts.

Particulary preferred compounds of formula I are those wherein $R_1$ is

and $R_2$ and $R_3$ are

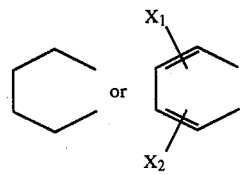

in which $X_1$ is hydrogen and $X_2$ is methoxy, isopropoxy or benzyloxy. Specific preferred compounds of formula I are (7-isopropoxy-imidazo[2,1-b]benzothiazol-2-yl) cyclopropyl-methanone; (7-methoxy-imidazo[2,1-b]benzothiazol-2-yl) cyclopropyl-methanone; (7-benzyloxy-imidazo[2,1-b]-benzothiazol-2-yl) cyclopropyl-methanone; and (5,6,7,8-tetrahydro-imidazo[2,1-b]benzothiazol-2-yl) cyclopropyl-methanone; and the acid addition salts thereof.

The novel process of the invention for the preparation of a compound of the formula

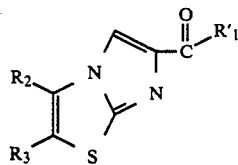

wherein $R_2$ and $R_3$ are as defined above and $R_1'$ is

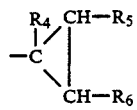

in which $R_4$ is hydrogen and $R_5$ and $R_6$ are individually hydrogen or alkyl of 1 to 5 carbon atoms or $R_1'$ is

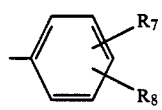

in which $R_7$ and $R_8$ are as defined above comprises oxidizing a compound of the formula

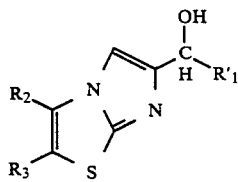

wherein $R_1'$, $R_2$ and $R_3$ are as defined above. The oxidation of the compound of formula IV is preferably effected with manganese dioxide, nitric acid, ferric chloride or chromium oxide in the presence of pyridine, or by the Oppenauer oxidation or by dehydrogenation in the presence of a copper catalyst.

The compounds of formula IV may conveniently be prepared by reacting a compound of the formula

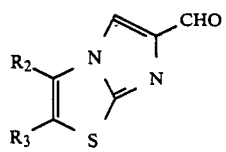

wherein $R_2$ and $R_3$ are as defined above with a compound of the formula

wherein M is an alkali metal atom such as lithium or —Mg—Hal in which Hal is chlorine, bromine or iodine and $R_1'$ is as defined above. The reaction of the compound of formula V with the compound of formula VI is preferably effected under anhydrous conditions in an organic solvent such as tetrahydrofuran.

The compounds of formula V may conveniently be prepared by oxidation of a compound of the formula

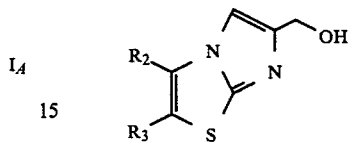

wherein $R_2$ and $R_3$ are as defined above. The oxidation of the compound of formula VII may advantageously be effected with manganese dioxide.

The compounds of formula VII may conveniently be prepared by: (i) Reaction of a compound of the formula

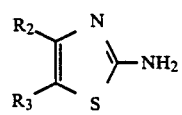

wherein $R_2$ and $R_3$ are as defined above with 3-bromo-1-hydroxypropan-2-one; or (ii) Reduction of a compound of the formula

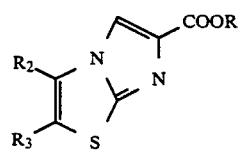

wherein $R_2$ and $R_3$ are as defined above and R is alkyl of 1 to 3 carbon atoms. The reduction is conveniently effected with lithium borohydride.

The 2-aminobenzothiazoles of formula VIII may be prepared as described in J. Het. Chem. (1980), Vol. 17, p 1325 and the 2-amino-4,5,6,7-tetrahydrobenzothiazoles of formula VIII may be prepared as described in J. Gen. Chem. USSR, Vol. 16, p 1701-5 (1946). The compounds of formula IX may be prepared as described in Farmaco Ed. Sci. (1977), Vol. 32, p 735.

The process of the invention for the preparation of compounds of the formula

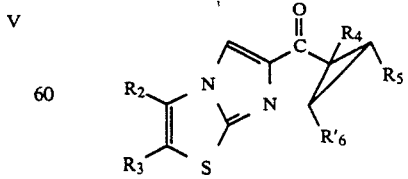

wherein $R_2$, $R_3$, $R_4$ and $R_5$ are as defined above and $R_6'$ is hydrogen, alkyl of 1 to 5 carbon atoms, phenyl, halogen or alkoxycarbonyl of 2 to 5 carbon atoms comprises reacting a compound of the formula

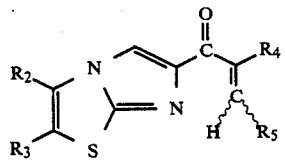

wherein $R_2$, $R_3$, $R_4$ and $R_5$ are as defined above with an appropriate cyclizing reagent. It will be understood that the cyclizing reagent will be a reagent serving to introduce —$CHR_6'$ across the vinylic double bond.

When a compound of formula $I_B$ wherein $R_4$ is alkyl of 1 to 5 carbon atoms and $R_5$ is hydrogen and $R_6'$ is hydrogen or alkyl of 1 to 5 carbon atoms is desired, the cyclization is advantageously effected with trialkylsulfoxonium iodide in the presence of an organic solvent such as dimethylformamide. When a compound of formula $I_B$ wherein $R_4$ is hydrogen and $R_5$ is alkyl of 1 to 5 carbon atoms, and $R_6'$ is hydrogen or alkyl of 1 to 5 carbon atoms is desired, the cyclization is advantageously effected with dimethylaminoalkylphenyloxosulfonium tetrafluoroborate in the presence of an organic solvent such as dimethylformamide.

When a compound of formula $I_B$ wherein $R_4$ and $R_5$ are hydrogen and $R_6$ is alkoxycarbonyl or phenyl is desired, the cyclization is advantageously effective with a dimethylsulfuranylidene alkyl acetate or benzyl dimethyl sulfonium anion in the presence of an organic solvent such as chloroform. When a compound of formula $I_B$ wherein $R_4$ and $R_5$ are hydrogen and $R_6'$ is halogen is desired, the cyclization is advantageously effected with a dimethylaminophenyloxosulfonium halogenomethyl ylide in the presence of an organic solvent such as dimethylformamide.

The compounds of formula X may, for example, be prepared by oxidizing a compound of the formula

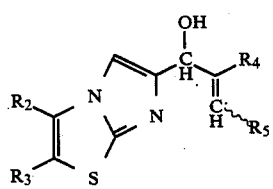

wherein $R_2$, $R_3$, $R_4$ and $R_5$ are defined as above.

Oxidation of the compound of formula XI is preferably effected with manganese dioxide, nitric acid, ferric chloride or chromium oxide in the presence of pyridine, or by the Oppenauer oxidation or by dehydrogenation in the presence of a copper catalyst.

The compounds of formula XI may, for example, be prepared for reacting a compound of the formula

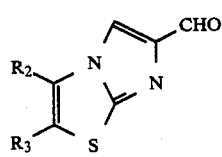

wherein $R_2$ and $R_3$ are as defined above with a compound of the formula

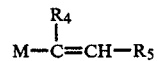

wherein M represents an alkali metal atom such as lithium or —Mg—Hal in which Hal is chlorine, bromine or iodine and $R_4$ and $R_5$ are as defined above. The reaction of the compound of formula V with the compound of formula XII is preferably effected under anhydrous conditions and in an organic solvent such as tetrahydrofuran.

The process of the invention for the preparation of compounds of the formula

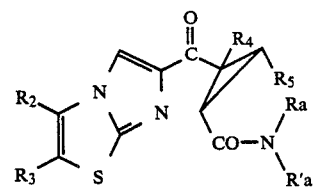

wherein $R_2$, $R_3$, $R_4$ and $R_5$ are as defined above and Ra and R'a are individually hydrogen or alkyl of 1 to 5 carbon atoms comprises reacting a compound of the formula

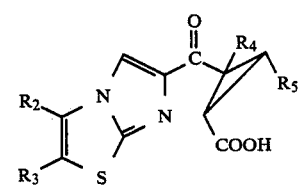

wherein $R_2$, $R_3$, $R_4$ and $R_5$ are as defined above with an amine of the formula

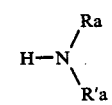

wherein Ra and R'a are as defined above. The reaction of the compound of formula I with the amine of formula XIII is preferably effected in the presence of an anhydrous organic solvent and in the presence of carbonyldiimidazole.

The compounds of formula $I_D$ may, for example, be prepared by saponification of a compound of the formula

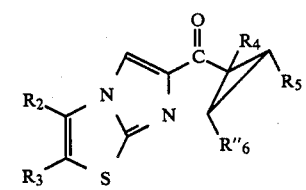

wherein $R_2$, $R_3$, $R_4$ and $R_5$ are as defined above and $R_6''$ is alkoxycarbonyl of 2 to 5 carbon atoms. The saponification of the compound of formula $I_B'$ is preferably effected with an alkali metal hydroxide such as sodium hydroxide.

The process of the invention for the preparation of a compound of the formula

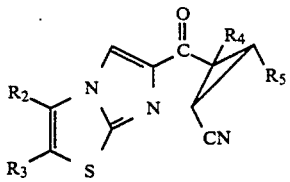

$I_E$ wherein $R_2$, $R_3$, $R_4$ and $R_5$ are as defined above comprises dehydrating a compound of the formula

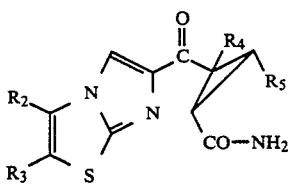

$I'_C$ wherein $R_2$, $R_3$, $R_4$ and $R_5$ are as defined above. The dehydration of the compound of formula $I_C'$ is preferably effected with the anhydride of a strong acid such as trifluoroacetic acid anhydride in the presence of an organic solvent such as dichloromethane.

The compounds of formula I are basic in character and may therefore, if desired, be subsequently converted into their acid addition salts. Advantageously, the acid addition salts of the compounds of formula I may be prepared by reacting in approximately stoichiometric proportions an inorganic or organic acid with the compound of formula I. The salts may be prepared without intermediate isolation of the corresponding base.

The novel compositions of the invention for treating memory disorders comprise an effective amount of at least one compound of formula I and their non-toxic, pharmaceutically acceptable acid addition salts and a pharmaceutical carrier. The compositions may be in the form of tablets, dragees, capsules, granules, suppositories and injectable solutions.

Examples of suitable excipients or carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions have weak to strong benzodiazepine inverse agonist properties depending on the substituents and some of the compounds also have tranquilizing properties. This means the compositions are useful in the treatment of memory disorders, particularly in geriatrics, and in cerebral senescence disorders. Some of the compounds may also be used in the treatment of obesity and as minor tranquillizers in the treatment of certain agitated or irritable conditions.

The novel method of the invention for the treatment of memory disorders in warm-blooded animals, including human, comprises administering to warm-blooded animals an amount of at least one compound of formula I and their non-toxic, pharmaceutically acceptable acid addition salts sufficient to treat memory disorders. The compounds may be administered orally, rectally or parenterally and the usual daily dose is 0.001 to 2.5 mg/kg depending upon the condition treated, the specific compound and the method of administration.

The following intermediates are also a part of the invention;

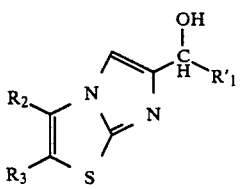

IV wherein $R_1'$, $R_2$ and $R_3$ are as defined above; the compounds of the formula

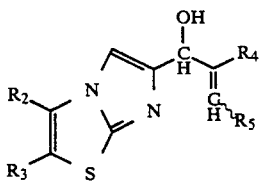

XI wherein $R_2$, $R_3$, $R_4$ and $R_5$ are as defined above; the compounds of the formula

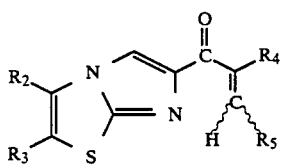

X wherein $R_2$, $R_3$, $R_4$ and $R_5$ are as defined above; and the compounds of the formula

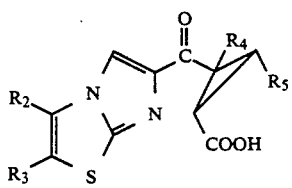

$I_D$ wherein $R_2$, $R_3$, $R_4$ and $R_5$ are as defined above.

In the following examples there are described several preferred embodiments to illustrate the invention. However, it should be understood that the invention is not intended to be limited to the specific embodiments.

EXAMPLE 1

(7-Methoxy-imidazo[2,1-b]benzothiazol-2-yl)-cyclopropylmethanone

STEP A: 7-Methoxy-imidazo[2,1-b]benzothiazol-2-methanol

A mixture of 11.6 g (0.069 mole) of 2-amino-5-methoxybenzothiazole and 11.6 g (0.076 mole) of 3-bromo-1-hydroxypropan-2-one in 120 ml of dry T.H.F. was stirred under nitrogen at 80° C. for 3 hours and the mixture was cooled in ice and the supernatant liquid decanted. The residue was heated in 60 ml of ethanol for 1 hour, cooled and filtered to give 7-methoxy-imidazo[2,1-b]benzothiazole-2-methanol hydrobromide as a pale yellow solid. The product was dissolved in water, made alkaline with aqueous sodium bicarbonate and was extracted 5 times with 200 ml of chloroform. The extracts were dried over magnesium sulfate, concentrated under reduced pressure and diluted with diethyl ether to obtain 6.30 g (42% yield) of 7-methoxy-imidazo[2,1-b]benzothiazole-2-methanol as colorless crystals melting at 202° to 205° C. (EtOH).

Analysis $C_{11}H_{10}N_2O_2S$:
Calculated: %C 56.40, %H 4.30, %N11.96, %S13.68,
Found: %C 56.32, %H 4.36, %N 11.93, %S 13.69.

STEP B:
7-Methoxy-imidazo[2,1-b]benzothiazole-2-carboxaldehyde 5.0 g (0.0225 mole) of the product of Step A and 10 g (0.115 mole) of manganese dioxide were stirred under reflux in 500 ml of chloroform for 2 hours. The mixture was filtered hot through celite and evaporated under reduced pressure to obtain 3.92 g (79% yield) of 7-methoxy-imidazo[2,1-b]benzothiazole-2-carboxaldehyde as colorless crystals melting at 214° to 215° C. (EtOH).

Analysi: $C_{11}H_8O_2N_2S$:
Calculated: %C 56.89, %H 3.47, %N 12.06, %S 13.80,
Found: %C 56.79, %H 3.56, %N 12.08, %S 13.75.

STEP C:
(7-Methoxy-imidazo[2,1-b]benzothiazol-2-yl)-cyclopropyl methanol A mixture of 3.6 g (0.03 mole) of cyclopropyl magnesium bromide prepared from cyclopropyl bromide and 0.8 g (0.033 mole) of magnesium in 50 ml of dry T.H.F. was added dropwise to a suspension of 3.9 g (0.0177 mole) of 7-methoxy-imidazo[2,1-b]benzothiazole-2carboxaldehyde in 80 ml of dry T.H.F. The mixture was stirred at room temperature for 3 hours and was quenched with saturated aqeous ammonium chloride solution. The mixture was extracted with ethyl acetate and the extracts were dried over magnesium sulfate and evaporated under reduced pressure. The residue was chromatographed on silica gel and eluted with 2% methanol/dichloromethane to obtain 2.75 g (69% yield) of [7-methoxy-imidazo[2,1-b]benzothiazol-2-yl) cyclopropyl methanol as colorless solid melting at 151° to 153° C.

Analysis: $C_{14}H_{14}N_2O_2S$:
Calculated: %C 61.30%, %H 5.14, %N 10.21, %S 11.69,
Found: %C 61.17, %H 5.23, %N 10.24, %C 11.48.

STEP D:
(7-Methoxy-imidazo[2,1-b]benzthiazol-2-yl)-cyclopropyl methanone A mixture of 1.63 g (0.0062 mole) of (7-methoxy-imidazo [2,1-b]benzothiazol-2-yl)-cyclopropyl methanol and 4.8 g (0.055 mole) of manganese dioxide was stirred under reflux in 300 ml of chloroform for 1 hour. The mixture was filtered hot and evaporated to dryness. Trituration with diethyl ether yielded 1.45 g (89% yield) of (7-methoxy-imidazo[2,1-b]benzothiazol-2-yl)-cyclopropyl methanone as a colorless solid melting at 213° as 214° C. (EtOH).

Analysis: $C_{14}H_{12}N_2O_2S$:
Calculated: %C 61.75, %H 4.44, %N 10.29, %S 11.77,
Found: %C 62.01, %H 4.49, %N 10.32, %S 11.76.

EXAMPLES 2 to 8

Using the method of Example 1, but starting from the corresponding compounds of formula V in which $R_2$ and $R_3$ have the definitions indicated in Table I, the compounds of Examples 2 to 8 were prepared. Yield, melting point, IR Spectrum and analytical data are given in Table I.

TABLE 1

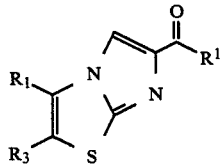

| Example | Yield % | $R^1$ | $R^2 R^3$ | mpt | I.R cm$^{-1}$ | | Analysis C% | H% | N% | S% |
|---|---|---|---|---|---|---|---|---|---|---|
| 1 | 89 | cyclopropyl | MeO | 213-4° | 3150 (C$_1$H), 1649 (C=O), 1618, 1518, 1507, 1488, 1377 | Found $C_{14}H_{12}N_2O_2S$ | 62.01 61.75 | 4.49 4.44 | 10.32 10.29 | 11.76 11.77 |
| 2 | 92 | cyclopropyl | H | 204-5° | 3160 (C$_1$H), 1650 (C=O), 1518 1502, 1374, 1209, 1050 | Found $C_{13}H_{10}N_2OS$ | 64.18 64.44 | 4.22 4.16 | 11.51 11.56 | 13.25 13.23 |
| 3 | 85 | cyclopropyl | MeO | 235-6° | 3140 (C$_1$H), 1651 (C=O), 1587, 1524br, 1423, 1374, 1286 | Found $C_{14}H_{12}N_2O_2S$ | 61.48 61.76 | 4.51 4.44 | 10.22 10.29 | 11.67 11.77 |
| 4 | 91 | cyclopropyl | PhCH$_2$O | 195-7° | 3160 (C$_1$H), 1651 (C=O), 1519, 1501, 1481, 1280, 1197 | Found $C_{20}H_{16}N_2O_2S$ | 68.70 68.95 | 4.70 4.63 | 8.01 8.04 | 9.15 9.20 |

TABLE 1-continued

![structure with R1, R3, N, N, S, O, R1]

| Example | Yield % | R¹ | R² R³ | mpt | I.R cm⁻¹ | Analysis | | C % | H % | N % | S % |
|---------|---------|----|----|-----|----------|----------|---|-----|-----|-----|-----|
| 5 | 75 | ◁— | (OCH₂O-benzodioxole) | 304–7° | 3140 (C₁H), 1655 (C=O), 1520, 1500, 1466, 1381, 1254 | Found $C_{14}H_{10}N_2O_3S$ | | 58.73 | 3.52 | 9.78 | 11.20 |
| 6 | 85 | ◁— | (cyclohexeno) | 182–4° | 3100 (C₁H), 1650 (C=O), 1512, 1443, 1378, 1311, 1234 | Found $C_{13}H_{14}N_2OS$ | | 63.52 63.39 | 5.78 5.73 | 11.59 11.73 | 12.95 13.02 |
| 7 | 85 | ◁— | Pr¹O— | 148–50° | 3120 (C₁H), 1650 (C=O), 1610, 1516, 1497, 1475, 1370, 1290 | Found $C_{16}H_{16}N_2O_2S$ | | 63.82 63.98 | 5.45 5.37 | 9.24 9.33 | 10.71 10.67 |
| 8 | 81 | ◁— | Me, Me | 286–8° | 3120 (C₁H), 1639 (C=O), 1500, 1362, 1295, 1187, 1160 | Found $C_{15}H_{14}N_2OS$ | | 66.47 66.64 | 5.29 5.22 | 10.30 10.36 | 11.89 11.86 |

The 6-methoxy-imidazo[2,1-b]benzothiazole-2-methanol used as starting material of Example 3 (compound of formula VII) was prepared as indicated below.

Preparation:
6-Methoxy-imidazo[2,1-b]benzothiazole-2-methanol

A mixture of 4.0 g of ethyl imidazo[2,1-b]benzothiazole-2-carboxylate in dry T.H.F. was stirred with 1.5 g of lithium borohydride for 48 hours at room temperature under dry nitrogen. The mixture was treated with an excess of 2N hydrochloric acid and warmed to 50° C. for 2 hours to decompose the complex. The mixture was made alkaline with aqueous sodium bicarbonate and extracted with ethyl acetate. The extracts were dried over magnesium sulfate and evaporated to dryness under reduced pressure to obtain 3.27 g (96.4% yield) of 6-methoxy-imidazo[2,1-b]benzothiazole-2-methanol as a colorless solid melting at 189° to 190° C. (EtOH).

Analysis: $C_{11}H_{10}N_2O_2S$:
Calculated: %C 56.40, %H 4.30, %N 11.96, %S 13.69,
Found: %C 56.37, %H 4.38, %N 11.90, %S 13.65.

EXAMPLE 9

Tablets were prepared containing 20 mg of the compound of Example 1 or 4 and sufficient excipient of lactose, starch, talc and magnesium stearate for a final weight of 150 mg.

Biochemical Activity

The affinity of the active ingredients for benzodiazepine receptors was measured using a radioactively labelled (³H) compound flunitrazepam in a modified version of the method of Squires et al [Nature, (1977), Vol. 266, p. 732]. The values given in Table 2 below are the concentration (mol × 10⁻⁹) of the compound under test which inhibited 50% of the specific binding of $0.6 \times 10^{-9}$ mol of ³H-labelled flunitrazepam in preparations of membrances from the rear portion of the brain in rats (IC₅₀ values).

TABLE 2

| EXAMPLE | Binding to Receptors |
|---------|---------------------|
|         | IC₅₀ nM             |
| 1 | 2.5 |
| 2 | 20 |
| 3 | 1000 |
| 4 | 3.2 |
| 5 | 158 |
| 6 | 79 |
| 7 | 6.3 |
| 8 | 60 |

Various modifications of the compounds and method of the invention may be made without departing from the spirit or scope thereof and it is to be understood that the invention is intended to be limited only as defined in the appended claims.

What we claim is:

1. A compound selected from the group consisting of a compound of the formula

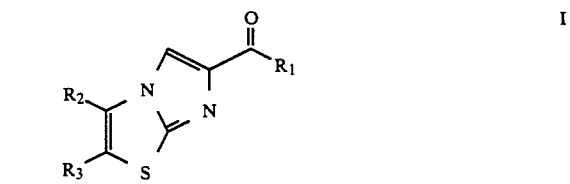

I wherein R₁ is selected from the group consisting of

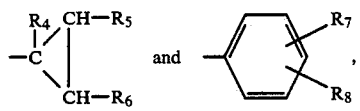 and 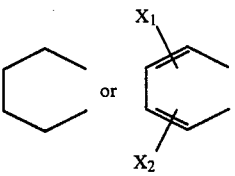

$R_4$, $R_5$, $R_7$ and $R_8$ are individually selected from the group consisting of hydrogen and alkyl of 1 to 5 carbon atoms, $R_6$ is selected from the group consisting of hydrogen, alkyl of 1 to 5 carbon atoms, phenyl, halogen, alkoxycarbonyl of 2 to 5 carbon atom, cyano,

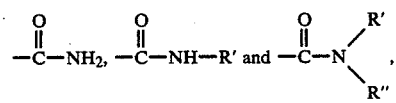

R' and R" are individually alkyl of 1 to 5 carbon atoms, $R_2$ and $R_3$ together form a member of the group consisting of

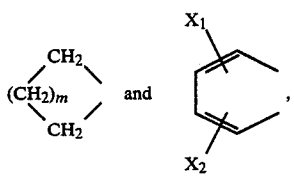

m is 1, 2 or 3, $X_1$ and $X_2$ are individually selected from the group consisting of hydrogen, alkyl of 1 to 5 carbon atoms, alkenyl of 2 to 5 carbon atoms, alkoxy of 1 to 5 carbon atoms, benzyloxy, phenethoxy, thienyloxy phenoxy and naphthoxy halogen, azido and nitro or taken together form methylenedioxy and their non-toxic, pharmaceutically acceptable acid addition salts.

2. A compound of claim 1 wherein $R_1$ is

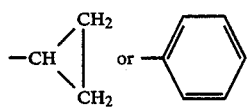

and $R_2$ and $R_3$ form

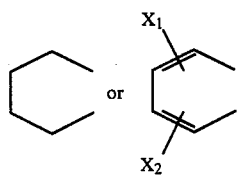

and $X_1$ and $X_2$ are individually selected from the group consisting of hydrogen, methyl, methoxy, isopropoxy and benzyloxy.

3. A compound of claim 1 or 2 wherein $R_1$ is

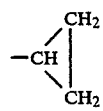

and $R_2$ and $R_3$ form and $X_1$ is hydrogen and $X_2$ is selected from the group consisting of methoxy, isopropoxy and benzyloxy.

4. A compound of claim 1 selected from the group consisting of (7-isopropoxy-imidazo[2,1-b]benzothiazol-2-yl) cyclopropyl-methanone and its non-toxic, pharmaceutically acceptable acid addition salts.

5. A compound of claim 1 selected from the group consisting of (7-methoxy-imidazo[2,1-b]benzothiazol-2-yl) cyclopropyl-methanone and its non-toxic, pharmaceutically acceptable acid addition salts.

6. A compound of claim 1 selected from the group consisting of (7-benzyloxy-imidazo[2,1-b]benzothiazol-2-yl) cyclopropyl-methanone and its non-toxic, pharmaceutically acceptable acid addition salts.

7. A compound of claim 1 selected from the group consisting of (5,6,7,8-tetrahydro-imidazo[2,1-b]benzothiazol-2-yl)-cyclopropyl-methanone and its non-toxic, pharmaceutically acceptable acid addition salts.

8. A compound having a formula selected from the group consisting of

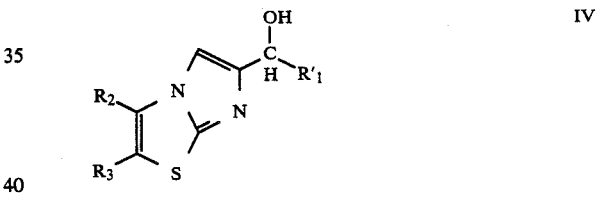    IV

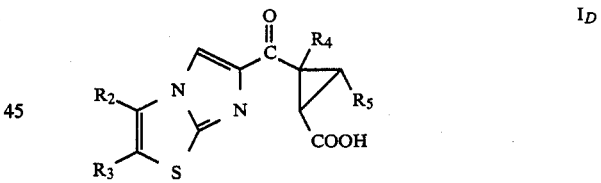    $I_D$ and

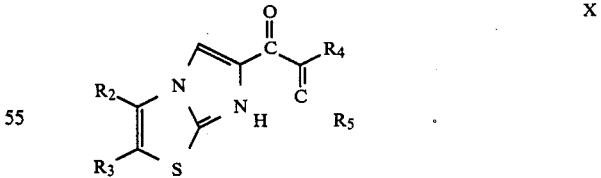    X

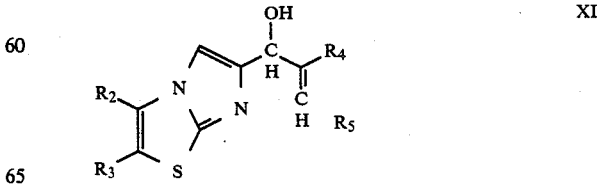    XI wherein $R_2$, $R_3$, $R_4$ and $R_5$ have the definition of claim 1 and $R_1'$ is

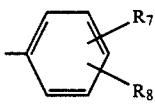

and R₇ and R₈ have the definition of claim 1.

9. A composition for treating memory disorders comprising an amount of at least one compound of claim 1 sufficient to treat memory disorders and a pharmaceutical carrier.

10. A composition of claim 9 wherein in the compound R₁ is

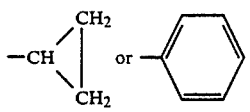

and R₂ and R₃ form

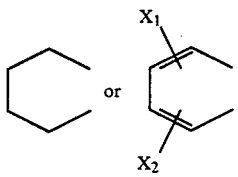

and X₁ and X₂ are individually selected from the group consisting of hydrogen, methyl, methoxy, isopropoxy and benzyloxy.

11. A composition of claim 9 or 10 wherein in the compound R₁ is

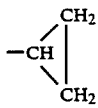

and R₂ and R₃ form

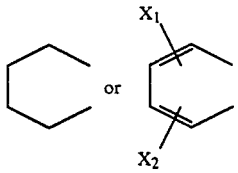

and X₁ is hydrogen and X₂ is selected from the group consisting of methoxy, isopropoxy and benzyloxy.

12. A composition of claim 9 wherein the active compound is selected from the group consisting of (7isopropoxy-imidazo[2,1-b]benzothiazol-2-yl)cyclopropyl-methanone and its non-toxic, pharmaceutically acceptable acid addition salts.

13. A composition of claim 9 wherein the active compound is selected from the group consisting of (7-methoxy-imidazo[2,1-b]benzothiazol-2-yl)-cyclopropyl-methanone and its non-toxic, pharmaceutically acceptable acid addition salts.

14. A composition of claim 9 wherein the active compound is selected from the group consisting of (7-benzyloxy-imidazo[2,1-b]benzothiazol-2-yl)-cyclopropyl-methanone and its non-toxic, pharmaceutically acceptable acid addition salts.

15. A composition of claim 9 wherein the active compound is selected from the group consisting of (5,6,7,8-tetrahydroimidazo[2,1-b]benzothiazol-2-yl)-cyclopropyl-methanone and its non-toxic, pharmaceutically acceptable acid addition salts.

16. A method of treating memory disorders in warm-blooded animals comprising administering to warm-blooded animals an amount of at least one compound of claim 1 sufficient to treat memory disorders.

17. A method of claim 11 wherein the compound R₁ is

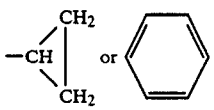

and R₂ and R₃ form

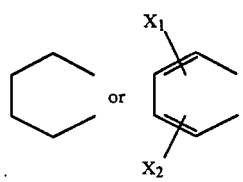

and X₁ and X₂ are individually selected from the group consisting of hydrogen, methyl, methoxy, isopropoxy and benzyloxy.

18. A method of claim 16 or 17 wherein in the compound R₁ is

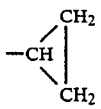

and R₂ and R₃ form

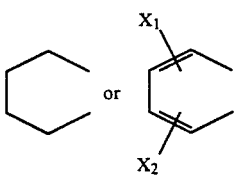

and X₁ is hydrogen and R₂ is selected from the group consisting of methoxy, isopropoxy and benzyloxy.

19. A method of claim 16 wherein the active compound is selected from the group consisting of (7-isopropoxy-imidazo[2,1-b]benzothiazol-2-yl)cyclopropyl-methanone and its non-toxic, pharmaceutically acceptable acid addition salts.

20. A method of claim 16 wherein the active compound is selected from the group consisting of (7-methoxy-imidazo[2,1-b]benzothiazol-2-yl)-cyclopropyl-methanone and its non-toxic, pharmaceutically acceptable acid addition salts.

21. A method of claim 11 wherein the active compound is selected from the group consisting of (7-benzyloxy-imidazo[2,1-b]benzothiazol-2-yl)-cyclopropyl-methanone and its non-toxic, pharmaceutically acceptable acid addition salts.

22. A method of claim 16 wherein the active compound is selected from the group consisting of (5,6,7,8-tetrahydroimidazo[2,1-b]benzothiazol-2-yl)-cyclopropyl-methanone and its non-toxic, pharmaceutically acceptable acid addition salts.

* * * * *